(12) United States Patent
Kopp

(10) Patent No.: US 11,045,174 B2
(45) Date of Patent: Jun. 29, 2021

(54) PATIENT MOVEMENT SENSOR

(71) Applicant: Covidien LP, Mansfield, MA (US)

(72) Inventor: Brock Kopp, Branford, CT (US)

(73) Assignee: COVIDIEN LP, Mansfield, MA (US)

( * ) Notice: Subject to any disclaimer, the term of this patent is extended or adjusted under 35 U.S.C. 154(b) by 430 days.

(21) Appl. No.: 15/758,934

(22) PCT Filed: Sep. 13, 2016

(86) PCT No.: PCT/US2016/051449
§ 371 (c)(1),
(2) Date: Mar. 9, 2018

(87) PCT Pub. No.: WO2017/053123
PCT Pub. Date: Mar. 30, 2017

(65) Prior Publication Data
US 2019/0038268 A1    Feb. 7, 2019

Related U.S. Application Data

(60) Provisional application No. 62/232,552, filed on Sep. 25, 2015.

(51) Int. Cl.
*A61B 17/00* (2006.01)
*A61B 5/11* (2006.01)
(Continued)

(52) U.S. Cl.
CPC ............. *A61B 17/00* (2013.01); *A61B 5/11* (2013.01); *A61B 5/1113* (2013.01);
(Continued)

(58) Field of Classification Search
CPC .......... A61B 17/00; A61B 5/11; A61B 34/30; A61B 5/1113; A61B 5/6801;
(Continued)

(56) References Cited

U.S. PATENT DOCUMENTS

| 4,660,829 A | * | 4/1987 | Whiteneir | A61B 5/1071 |
| | | | | 473/202 |
| 5,236,144 A | * | 8/1993 | Kautz | B65H 75/48 |
| | | | | 242/371 |

(Continued)

FOREIGN PATENT DOCUMENTS

| EP | 1138286 A2 | 10/2001 |
| WO | 2013164770 A2 | 11/2013 |

OTHER PUBLICATIONS

International Search Report and Written Opinion for Int'l Appln. No. PCT/US2016/051449 dated Dec. 8, 2016.

*Primary Examiner* — Devin B Henson
*Assistant Examiner* — Joseph A Tombers

(57) ABSTRACT

A motion sensor for detecting the movement of a patient is provided and includes a housing, a spring loaded return mechanism supported in the housing, an encoder, and a sensor. The spring loaded return mechanism includes a spool rotatably supported within the housing, a biasing member coupled to the housing and the spool, and a cord supported on the spool. The encoder is located on the spool and is configured to monitor a length of cord extended from the housing. The sensor is configured to communicate a signal when the cord is extended beyond a predetermined or preset length.

10 Claims, 3 Drawing Sheets

(51) Int. Cl.
*A61B 34/30* (2016.01)
*A61B 5/00* (2006.01)
*A61B 90/00* (2016.01)
*A61B 34/20* (2016.01)

(52) U.S. Cl.
CPC .......... *A61B 5/6801* (2013.01); *A61B 5/6891* (2013.01); *A61B 34/30* (2016.02); *A61B 2017/00694* (2013.01); *A61B 2034/2059* (2016.02); *A61B 2090/061* (2016.02); *A61B 2090/067* (2016.02); *A61B 2090/0807* (2016.02); *A61B 2505/05* (2013.01); *A61B 2562/0219* (2013.01)

(58) Field of Classification Search
CPC ............ A61B 5/6891; A61B 2090/061; A61B 2034/2059; A61B 2090/067; A61B 2090/0807; A61B 2017/00694; A61B 2505/05; A61B 2562/0219; G01B 3/11
See application file for complete search history.

(56) References Cited

U.S. PATENT DOCUMENTS

| | | |
|---|---|---|
| 5,552,771 A | 9/1996 | Leyden et al. |
| 6,353,314 B1 | 3/2002 | Moerbe |
| 6,689,074 B2 * | 2/2004 | Seto .................. A61F 2/54 601/33 |
| 7,197,974 B2 | 4/2007 | Glasson |
| 8,220,676 B1 | 7/2012 | Hicks |
| 8,604,927 B2 | 12/2013 | Sisney |
| 8,701,833 B2 | 4/2014 | Marquardt et al. |
| 8,828,023 B2 | 9/2014 | Neff et al. |
| 8,955,732 B2 | 2/2015 | Zemlok et al. |
| 2009/0009319 A1 * | 1/2009 | Yu ..................... H04Q 9/00 340/539.12 |
| 2009/0031823 A1 | 2/2009 | Doh et al. |
| 2012/0203140 A1 * | 8/2012 | Malchau .............. A61B 5/0022 600/595 |
| 2015/0077765 A1 | 3/2015 | Pettersson |
| 2015/0320514 A1 * | 11/2015 | Ahn ..................... A61B 34/30 606/130 |

* cited by examiner

PATIENT MOVEMENT SENSOR

CROSS-REFERENCE TO RELATED APPLICATIONS

This application is a U.S. National Stage Application filed under 35 U.S.C. § 371(a) of International Patent Application Serial No. PCT/US2016/051449, filed Sep. 13, 2016, which claims the benefit of and priority to U.S. Provisional Patent Application Ser. No. 62/232,552, filed Sep. 25, 2015, the entire disclosure of which is incorporated by reference herein.

BACKGROUND

In robotic surgical systems, a robot is typically affixed to a specific location for the entirety of the surgical procedure and programmed to operate on the patient through a predetermined tissue access point known as the remote center of motion. The robot assumes that the remote center of motion does not change, even if the patient moves on the surgical table during the procedure. As such, if the patient's movement is not accounted for, the robot may operate in an incorrect location or may exert undeserved pressure on the anatomy (e.g., abdominal wall) of the patient.

Accordingly, a need exists for a patient monitoring sensor that could be used to detect patient movement on a surgical bed.

SUMMARY

In accordance with an aspect of the present disclosure, a motion sensor for detecting the movement of a patient is provided. The motion sensor includes a housing having a first attachment portion, a spring loaded return mechanism supported in the housing, an encoder, and a sensor. The spring loaded return mechanism includes a spool rotatably supported within the housing, a biasing member coupled to the housing and the spool, and a cord supported on the spool, the cord having a first end and a second end, the first end of the cord coupled to the spool and the second end of the cord having a second attachment portion, wherein the second attachment portion of the cord is extendable such that the spool is rotated about the housing. The encoder is located on the spool and is configured to monitor a length of cord extended from the housing. The sensor is configured to communicate a signal when the cord is extended beyond a predetermined or preset length.

In one embodiment, the motion sensor may further include a gyroscope configured to measure an angle of a longitudinal axis of a patient relative to a preset longitudinal axis.

In one embodiment, the first attachment portion of the housing of the motion sensor is configured to be attached to a surgical table and the second attachment portion of the cord of the motion sensor is configured to be attached to a patient.

In one embodiment, the encoder is located coaxially around the spool.

In one embodiment, the encoder is configured to convert an angular position of the spool into a distance traveled by the cord.

In one embodiment, when the first attachment portion of the housing is attached to the surgical table and when the second attachment portion of the cord is attached to a patient, the encoder calculates an initial distance traveled by the cord.

In accordance with an aspect of the present disclosure, a method for performing robotic surgery is provided. The method including the steps of placing a patient on a surgical table, operably coupling a motion sensor to the patient and the surgical table, recording a position of the patient on the surgical table with respect to the motion sensor, initiating a surgical procedure, and monitoring the position of the patient on the surgical table with respect to the motion sensor.

In one embodiment of the method, coupling a motion sensor to the patient and the surgical table includes, attaching a first attachment portion of a housing of the motion sensor to the surgical table and attaching a second attachment portion of a cord extending from the housing of the motion sensor to the patient.

In one embodiment of the method, recording a position of the patient on the surgical table with respect to the motion sensor includes, measuring a distance traveled by the cord between the housing of the motion sensor to the patient.

In one embodiment of the method, further including setting an incline angle for the surgical bed with respect to a longitudinal axis.

In one embodiment of the method, further including defining a tissue access point on a patient for a surgical instrument.

In one embodiment of the method, monitoring the position of the patient on the surgical table with respect to the motion sensor includes, resetting a tissue access point on the patient and defining a new tissue access point on a patient for the surgical instrument.

In one embodiment of the method, monitoring the position of the patient on the surgical table with respect to the motion sensor includes, stopping the surgical procedure when the location of the patient is beyond a predetermined limit.

BRIEF DESCRIPTION OF THE DRAWINGS

Embodiments of the present disclosure are described herein with reference to the accompanying drawings, wherein.

DETAILED DESCRIPTION

Figure 1:
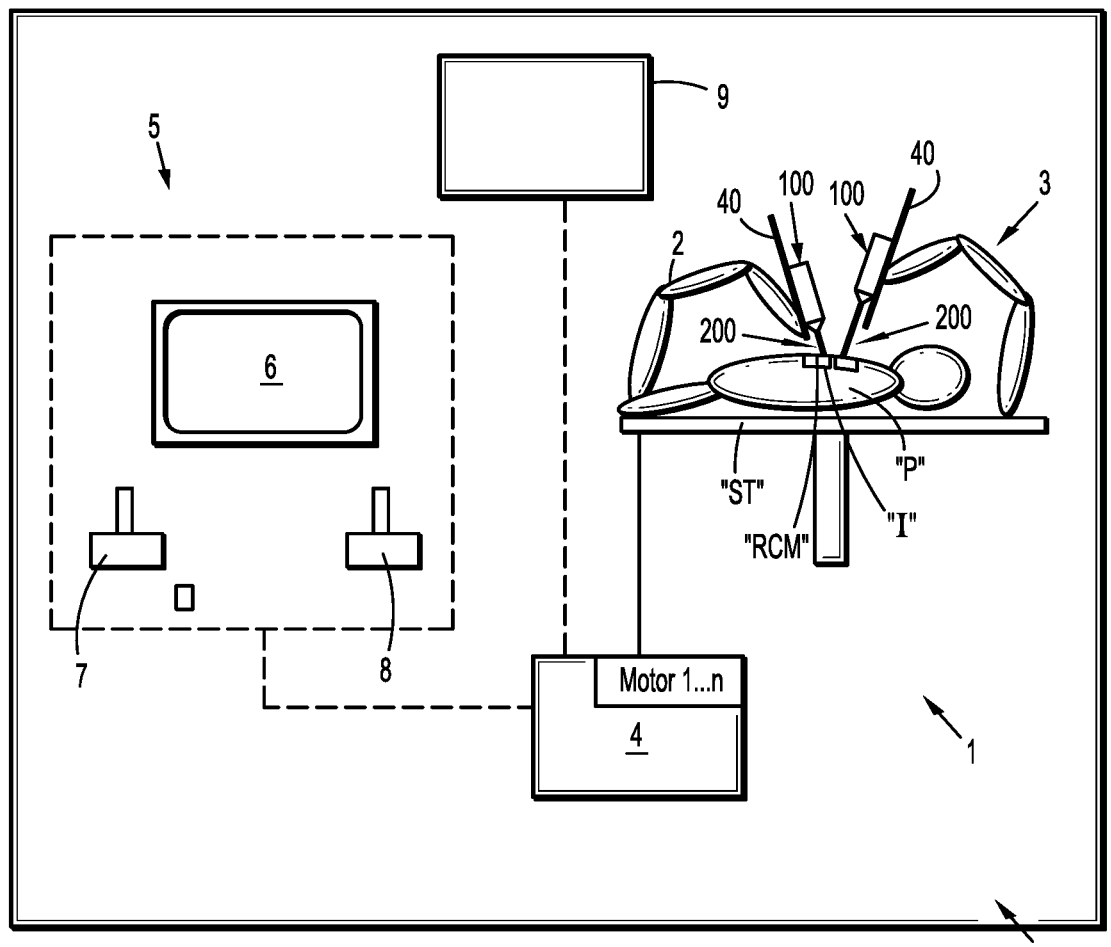
FIG. 1 is a schematic illustration of a robotic surgical system including a robotic surgical assembly in accordance with the present disclosure.

Embodiments of the presently disclosed surgical assembly including an instrument drive unit for driving the operation of an electromechanical surgical instrument and methods thereof are described in detail with reference to the drawings, in which like reference numerals designate identical or corresponding elements in each of the several views. As used herein the term "distal" refers to that portion of the robotic surgical system, surgical assembly, or component thereof, that is further from the user, while the term "proximal" refers to that portion of the robotic surgical system, surgical assembly, or component thereof, that is closer to the user.

As will be described in detail below, provided is a motion sensor configured to track and locate a patient on a surgical table. Additionally, provided is a feedback assembly configured to determine the location of the patient on the surgical table and automatically adjust the location of the point of entry on the patient, i.e. remote center of motion, for a given operation.

Referring initially to FIG. 1, a surgical system, such as, for example, a robotic surgical system 1 is shown. In embodiments, robotic surgical system 1 is located in an operating room "OR." Robotic surgical system 1 generally includes a plurality of surgical robotic arms 2, 3 having a robotic surgical assembly 100 and an electromechanical surgical instrument 200 removably attached to a slide rail 40 of surgical robotic arms 2, 3; a control device 4; and an operating console 5 coupled with control device 4. In embodiments, the robotic surgical system 1 may include an overhead camera 9 configured to record and monitor the procedure taking place in the operating room "OR."

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached robotic surgical assembly 100, and thus electromechanical surgical instrument 200 (including the electromechanical end effector, not shown) execute a desired movement according to a movement defined by means of manual input devices 7, 8. Control device 4 may also be set up in such a way that it regulates the movement of robotic arms 2, 3 and/or of a surgical instrument, e.g., electromechanical surgical instrument 200, as detailed below.

In particular, control device 4 may be configured to assign a tissue access point or a remote center of motion (hereinafter "RCM") through which electromechanical surgical instrument 200 must pass when operating on a patient "P" lying on a surgical table "ST." The "RCM" is a point in space corresponding to a center of an incision "I" in patient "P." It is contemplated that the movement of robotic arms 2 and 3 may be regulated if a centerline (not shown) of the electromechanical surgical instrument 200 is constrained to pass through the "RCM" of patient "P."

Robotic surgical system 1 may also include more than two robotic arms 2, 3, the additional robotic arms likewise being connected to control device 4 and being telemanipulatable by means of operating console 5. A surgical instrument, for example, electromechanical surgical instrument 200 (including the electromechanical end effector), may also be attached to the additional robotic arm. Further, it is contemplated that each robotic arm may have its own "RCM" to which it is constrained to operate.

In other embodiments, robotic surgical system 1 may include only one robotic arm configured to be used, for example, as a scope holder or the like. In this embodiment, a surgeon or user may adjust the positioning of the robotic arm manually, without the use of telemanipulation.

For a detailed discussion of the construction and operation of a robotic surgical system, reference may be made to U.S. Pat. No. 8,828,023, filed on Nov. 3, 2011, entitled "Medical Workstation," the entire contents of which are incorporated by reference herein.

Figure 2:
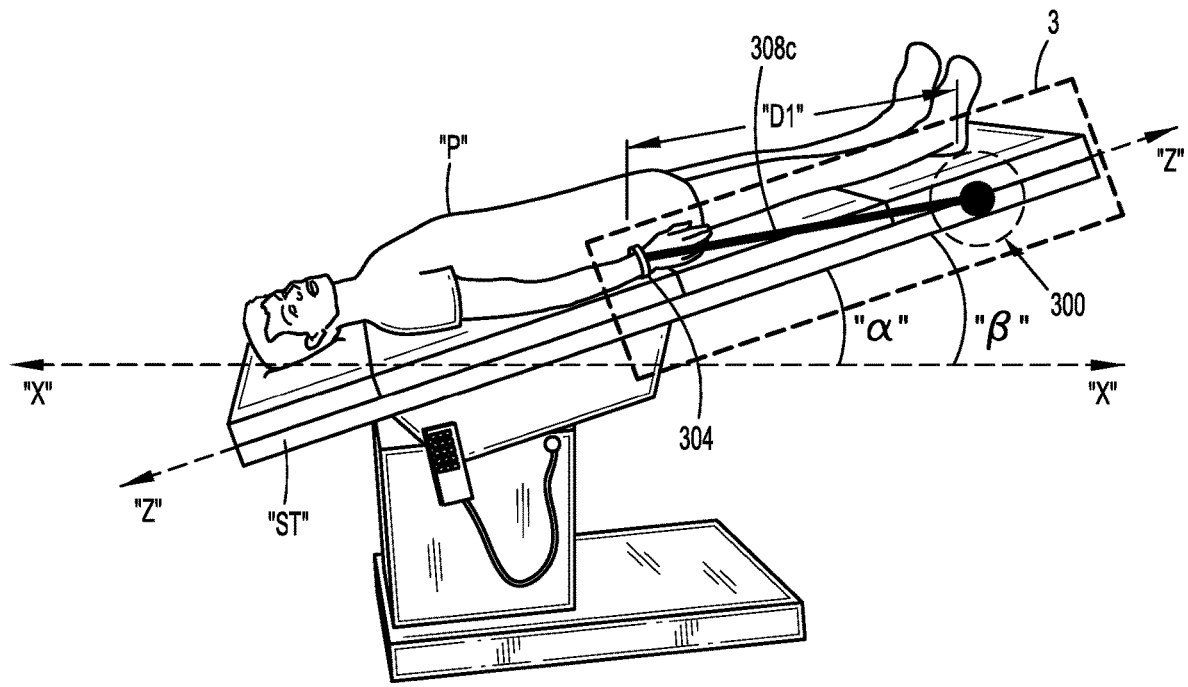
FIG. 2 is side view of a patient located on a surgical table of the robotic surgical system of claim 1.
Figure 3:
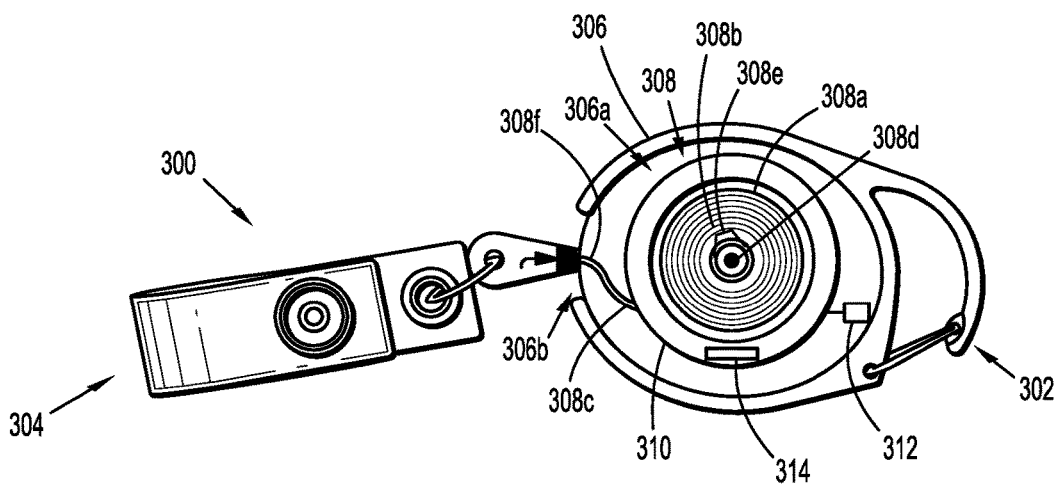
FIG. 3 an enlarged view of the indicated area of detail of FIG. 2.
Figure 4:
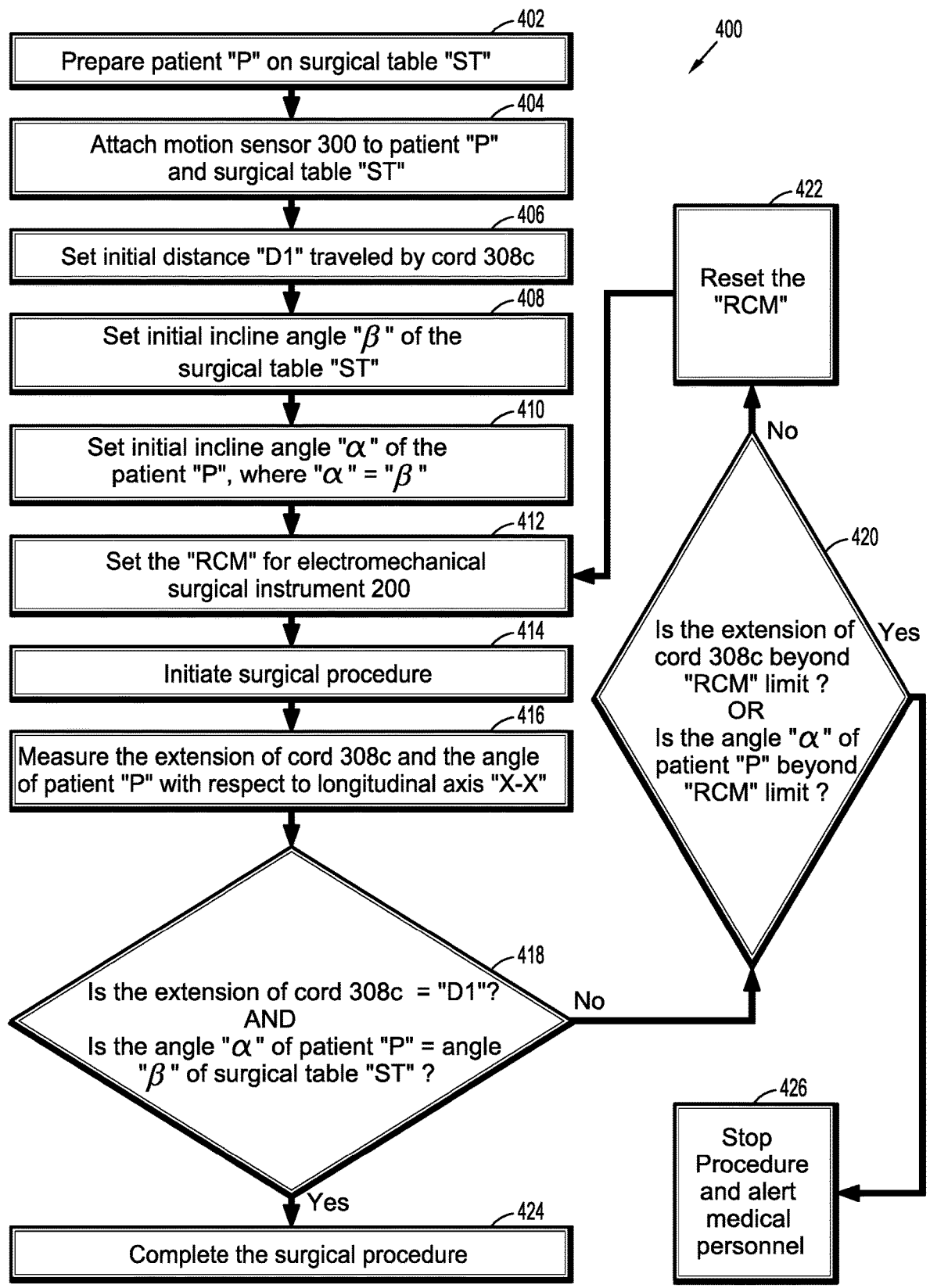
FIG. 4 is a flow chart showing a method of locating and maintaining a location of a patient on a surgical table according to embodiments of the present disclosure.

Turning now to FIGS. 2-4, in embodiments, the surgical table "ST" may be inclined such that patient "P" is in the Trendelenburg position (see FIG. 2) or in the reverse Trendelenburg position (not shown). As shown in FIG. 2, a motion sensor assembly 300 may be secured to the surgical table "ST" at a first attachment portion 302 and secured to patient "P" at a second attachment portion 304. Motion sensor assembly 300 is configured to detect incremental movement of patient "P" about surgical table "ST."

With reference to FIGS. 2 and 3, motion sensor assembly 300 includes a housing 306 having a first attachment portion 302. In embodiments, first attachment portion 302 may be a clip-on attachment as shown in FIG. 3. However, it is contemplated that any suitable attachment mechanism, such as, for example, adhesives, screws, fasteners, hook and loops type features or magnets, may be used.

Continuing with FIG. 3, housing 306 defines a cavity 306a configured for supporting a return mechanism 308. Return mechanism 308 includes a spool 308a, a biasing member 308b, and a cord 308c wound around spool 308a.

In embodiments, spool 308a is rotatably supported on a pivot 308d and resiliently biased by biasing member 308b to rotate about pivot 308d (e.g., in a counter-clockwise direction given by arrow "A"). In embodiments, biasing member 308b is a power spring or a coil spring or a torsion spring having a first end (not shown) fixed to the pivot 308d and a second end (not shown) fixed the spool 308a. As such, for example, when spool 308a is rotated about pivot 308d in a clockwise direction given by arrow "B," biasing member or power spring 308b tightly coils around pivot 308d creating potential energy. When spool 308a is released, power spring 308b unwinds and rotates spool 308a about pivot 308d in the counter-clockwise direction given by arrow "A." It is contemplated that power spring 308b is only disclosed as an example of biasing member 308b. As such, biasing member 308b may be any spring, suitable for the purposes detailed herein.

As noted above, return mechanism includes cord 308c supported on spool 308a. In particular, cord 308c includes a first end 308e fixed to spool 308a. Cord 308c is configured to wrap around spool 308a relative to the first end 308e. Cord 308c also includes a second end 308f configured to extend from an opening 306b of housing 306. The second end 308f of cord 308c includes the second attachment portion 304. In embodiments, the second attachment portion 304 may be a hook-and-loop wrist band as shown in FIG. 2 or a snap on attachment as shown in FIG. 3. It is also contemplated that the second attachment portion 304 may be an adhesive pad or a clip for connection directly to the patient "P" or to the gown of patient "P." Though examples of second attachment portion 304 have been disclosed herein, it is contemplated that any attachment device, suitable for the purposes detailed herein, may be used.

Turning briefly to FIG. 2, though it is illustrated that the first attachment portion 302 is fixed to the surgical table "ST" and the second attachment portion 304 is fixed to the patient "P," other embodiments or methods of use are also contemplated. For example, in embodiments, the first attachment portion 302 may be fixed to a stationary structure in the operating room "OR" while the second attachment portion may be fixed to the surgical table "ST." This embodiment may be used to monitor the movement or the tilt of the surgical table "ST" about the operating room "OR."

Returning to FIG. 3, the motion sensor assembly 300 also includes an encoder 310 supported within cavity 306a of housing 306. In embodiments, encoder 310 may be coaxially located around spool 308a. However, it is also contemplated that encoder 310 may be disposed in any location suitable for the purposes detailed herein.

Encoder 310 is configured to convert an angular position of spool 308a into data which may be processed into a distance traveled. For example, when cord 308c is extended out of housing 306 and spool 308a is rotated proportionally, encoder 310 is configured to convert the rotation of spool 308a into data which may be processed into the distance traveled by cord 308c. Moreover, encoder 310 is configured to communicate this data to a sensor 312. In embodiments, when cord 308c is extended beyond a user-defined limit "D1," which may mean that patient "P" is slipping down the surgical table "ST," sensor 312 is configured to communicate a signal e.g., an alarm, to alert the medical personal of the patient "P's" movement.

For a detailed discussion of suitable encoders, reference may be made to U.S. Pat. No. 8,955,732, filed on Mar. 19, 2012, entitled "Surgical Stapling Apparatus," the entire contents of which are incorporated by reference herein.

In embodiments, encoder 310 may also include a gyroscope 314 or the like as shown in FIG. 3. Gyroscope 314 is configured to measure an angle "α." In particular, gyroscope 314 is configured to measure the angle "α" between a longitudinal axis "X-X" and the inclined position of the patient "P" given by an axis "Z-Z." When patient "P" is in a desired position, angle "α" will be equal to a predetermined incline angle "β" of the surgical table "ST." However, if angle "α" is different from angle β," sensor 312 may similarly be configured to communicate a signal e.g., an alarm, to alert the medical personal of the patient "P's" movement.

In embodiments, along with alerting the medical personal of the patient "P's" movement, sensor 312 may also be configured to communicate the location of patient "P," based on the data received from encoder 310 and gyroscope 314, to the robotic surgical system 1 shown in FIG. 1.

As noted above with reference to FIG. 1, control device 4 may be configured to constrain the movement of robotic arms 2, 3 and the trajectory of electromechanical surgical instrument 200 by assigning an "RCM" to each of the robotic arms 2, 3 and their respective electromechanical surgical instrument 200. Typically, the "RCM" of the robotic arms 2, 3 do not change once it is assigned. However, if the location of patient "P" changes, the original "RCM" may no longer be the center of the incision "I." Therefore, continuing to operate through the original "RCM" is undesired.

In embodiments as shown in FIG. 4, it is contemplated that the location of patient "P" may be used to automatically update the "RCM" for robotic arms 2, 3 and electrosurgical instrument 200 using a process 400. In embodiments, the location of patient "P" may also be used to automatically stop the surgical procedure and alert medical personal if the location of patient "P" is beyond a limit where resetting the "RCM" of the robotic arms 2, 3 and electrosurgical instrument 200 would not be useful or desired. It is contemplated that this limit is a predetermined limit based on the movement trajectory constraints of robotic arms 2, 3 and electrosurgical instrument 200.

With reference to FIGS. 1-4, in operation, process 400 includes a first step 402, where patient "P" is prepared on surgical table "ST." Step 402 may include any suitable preoperative procedures, such as, for example, administering anesthetics to patient "P."

Next, in step 404, motion sensor 300 is attached to the surgical table "ST" at the first attachment portion 302 and attached to patient "P" at the second attachment portion 304. In step 406, the user-defined distance "D1" of cord 308c is set as the distance between housing 306 of motion sensor 300 and second attachment portion 304 of motion sensor 300. In embodiments, after setting the user-defined distance "D1," the encoder 310 may be zeroed out at distance "D1." This way, if the patient "P" moves, encoder 310 would be configured to record the distance that patient "P" traveled beyond the distance "D1." In alternative embodiments, the encoder 310 may be configured to record both the initial user defined distance "D1" as well as the new location of patient "P."

In step 408, the surgical table "ST" is inclined to a predetermined angle "β" with respect to the longitudinal axis "X-X." In step 410, the angle "α" of patient "P" is set with respect to the longitudinal axis "X-X." It is contemplated that initially, angle "α" of patient "P" should be equal to angle "β" of the surgical table "ST." In step 412, based on the initial location of patient "P," the "RCM" for each electromechanical surgical instrument 200 of robotic arms 2, 3 are set, using control device 4. Then in step 414, the surgical procedure is initiated.

Throughout the surgical procedure, as shown in step 416, the encoder 310 and gyroscope 314 measures and monitors the extension of cord 308c and the angle of patient "P" with respect to the longitudinal axis "X-X," respectively. During this step the extension of cord 308c is measured by encoder 310, and the angle "α" of patient "P" is measured by gyroscope 314. In step 418, if the extension of cord 308c is equal to the initial distance "D1" and the angle "α" of patient "P" is equal to the angle "β" of the surgical table "ST," the surgical procedure is continued or completed as shown in step 424. However, if either of these questions in step 418 is answered in the negative, step 420 is initiated to determine whether either the extension of cord 308c or the angle "α" of patient "P" is beyond the "RCM" limit. The "RCM" limit is a predetermined limit based on the movement constraints of robotic arms 2, 3 and the trajectory of electromechanical surgical instrument 200. As such, if the location of patient "P" is beyond the movement constraints of robotic arms 2, 3 and electromechanical surgical instrument 200, the location of patient "P" is beyond the "RCM" limit. If either question in step 420 is answered in the affirmative, meaning if either parameter is beyond the "RCM" limit, the 426 is initiated to stop the surgical procedure and alert the medical personal. However, if neither question is answered in the affirmative, meaning that neither parameter is beyond the "RCM" limit, the "RCM" is reset as shown in step 422. Then the process loops back to step 412 where the control device 4 is used to set the "RCM" for each electromechanical surgical instrument 200 of robotic arms 2, 3, or the location of the patient "P" is reset. This process is looped throughout the surgical procedure until step 418 is answered in the affirmative and the surgical procedure is completed as shown in step 424.

It will be understood that various modifications may be made to the embodiments disclosed herein. For example, in embodiments, camera 9 in the operating room "OR" may be configured to be used alone, or in conjunction with encoder 310 and gyroscope 314 of motion sensor 300 to locate patient "P" to automatically update the "RCM" in the event that patient "P" moves relative to the surgical table "ST." Therefore, the above description should not be construed as limiting, but merely as exemplifications of various embodi-

The invention claimed is:

1. A motion sensor for detecting the movement of a patient, the motion sensor comprising:
    a housing having a first attachment portion;
    a spring loaded return mechanism supported in the housing, the spring loaded return mechanism including:
        a spool rotatably supported within the housing;
        a biasing member coupled to the housing and the spool; and
        a cord supported on the spool, the cord having a first end and a second end, the first end of the cord coupled to the spool and the second end of the cord having a second attachment portion including a patient-engaging element, wherein the second end of the cord is extendable such that the spool is rotated about the housing;
    an encoder located on the spool, the encoder configured to monitor a length of cord extended from the housing;
    a sensor configured to communicate a signal when the cord is extended beyond a predetermined or preset length; and
    a gyroscope disposed in mechanical cooperation with the encoder and configured to measure an angle of a longitudinal axis of a patient relative to a preset longitudinal axis.

2. The motion sensor according to claim 1, wherein the first attachment portion of the housing of the motion sensor is configured to be attached to a surgical table and the second attachment portion of the cord of the motion sensor is configured to be attached to a patient.

3. The motion sensor according to claim 1, wherein the encoder is located coaxially around the spool.

4. The motion sensor according to claim 1, wherein the encoder is configured to convert an angular position of the spool into a distance traveled by the cord.

5. The motion sensor according to claim 2, wherein the encoder is configured to calculate an initial distance traveled by a patient.

6. The motion sensor according to claim 1, wherein the patient-engaging element includes a wrist band.

7. The motion sensor according to claim 6, wherein the wrist band includes a hook-and-loop portion.

8. The motion sensor according to claim 1, wherein the patient-engaging element includes a snap on attachment portion.

9. The motion sensor according to claim 1, wherein the patient-engaging element includes an adhesive pad.

10. A motion sensor for detecting the movement of a patient, the motion sensor comprising:
    a housing having a first attachment portion;
    a spring loaded return mechanism supported in the housing, the spring loaded return mechanism including:
        a spool rotatably supported within the housing;
        a biasing member coupled to the housing and the spool; and
        a cord supported on the spool, the cord having a first end and a second end, the first end of the cord coupled to the spool and the second end of the cord having a second attachment portion, wherein the second end of the cord is extendable such that the spool is rotated about the housing;
    an encoder located on the spool, the encoder configured to monitor a length of cord extended from the housing;
    a sensor configured to communicate a signal when the cord is extended beyond a predetermined or preset length; and
    a gyroscope disposed in mechanical cooperation with the housing and configured to measure an angle of a longitudinal axis of a patient relative to a preset longitudinal axis.

* * * * *